United States Patent [19]

Buell

[11] Patent Number: 4,578,071

[45] Date of Patent: Mar. 25, 1986

[54] DISPOSABLE ABSORBENT ARTICLE HAVING AN IMPROVED LIQUID MIGRATION RESISTANT PERIMETER CONSTRUCTION

[75] Inventor: Kenneth B. Buell, Cincinnati, Ohio

[73] Assignee: The Procter & Gamble Company, Cincinnati, Ohio

[21] Appl. No.: 689,279

[22] Filed: Jan. 7, 1985

Related U.S. Application Data

[63] Continuation of Ser. No. 463,182, Feb. 2, 1983, abandoned, which is a continuation-in-part of Ser. No. 237,785, Feb. 24, 1981, abandoned.

[51] Int. Cl.[4] ............................................. A61F 13/16
[52] U.S. Cl. .................................. 604/379; 604/385 R
[58] Field of Search ................ 604/385, 379, 380, 358

[56] References Cited

U.S. PATENT DOCUMENTS

| | | | |
|---|---|---|---|
| 3,520,303 | 7/1970 | Endres | 604/385 |
| 3,636,952 | 1/1972 | George | 604/385 |
| 3,665,921 | 5/1972 | Stumpf | 604/385 |
| 3,965,906 | 6/1976 | Karami | 604/385 |
| 4,015,604 | 4/1977 | Csillag | 604/385 |
| 4,285,342 | 8/1981 | Mesek | 604/385 |

*Primary Examiner*—John D. Yasko
*Attorney, Agent, or Firm*—John M. Pollaro; Fredrick H. Braun; Richard C. Wittie

[57] ABSTRACT

An article of manufacture is disclosed for absorbing liquids, particularly body fluids such as urine. A liquid permeable topsheet is affixed to a liquid impermeable backsheet encasing an absorbent core therebetween. A liquid impermeable barrier member overlays a segment of the absorbent core and is affixed at one end to the backsheet. The topsheet has compacted portions which are affixed to the barrier member.

10 Claims, 4 Drawing Figures

DISPOSABLE ABSORBENT ARTICLE HAVING AN IMPROVED LIQUID MIGRATION RESISTANT PERIMETER CONSTRUCTION

CROSS REFERENCE TO RELATED APPLICATION

This is a continuation of application Ser. No. 463,182, filed on Feb. 2, 1983, now abandoned, which in turn is a continuation in part of application Ser. No. 237,785 filed Feb. 24, 1981, now abandoned.

BACKGROUND OF THE INVENTION

This invention relates to disposable absorbent articles generally and more particularly relates to disposable diapers and the like. Still more particularly, this invention relates to disposable diapers having a topsheet in which compacted portions of the topsheet are adhered to barrier members at the perimeter of the absorbent core thereby providing a liquid migration resistant perimeter construction.

Disposable absorbent articles are well known in the prior art and have many uses. For example, disposable diapers are intended to absorb and contain urine; bandages are intended to absorb and contain blood and other body exudates; while catamenial pads are intended to absorb and retain menstrual fluids. In each instance, the disposable absorbent article absorbs and retains a liquid, thereby preventing that liquid from soiling, wetting, or otherwise contaminating the vicinity surrounding the point of liquid discharge.

In general, disposable absorbent articles all have the same basic structure which comprises an absorbent core encased between a liquid permeable user contacting topsheet and a liquid impermeable backsheet. The prior art teaches numerous variations of and elements in addition to the basic topsheet, backsheet, and absorbent core arrangement, with each variation or additional element being directed to improving a specific characteristic of the disposable absorbent article.

Ideally, a disposable absorbent article will have characteristics which permit liquid to rapidly penetrate the liquid permeable user contacting topsheet while large quantities of liquid are absorbed by the absorbent core. Once in contact with the absorbent core, the liquid will tend to migrate or spread away from the point of discharge. Accordingly, the liquid will migrate throughout the thickness of and toward the perimeter of the absorbent core. Liquid which penetrates the thickness of the core is prevented from wetting the vicinity surrounding the diaper by the liquid impermeable backsheet.

Several concepts have been proposed to prevent the liquid which migrates toward the perimeter of the diaper from wetting the wearer's undergarments. For example, U.S. Pat. No. 3,520,303 which issued to D. D. Endres on July 14, 1970 teaches a disposable diaper having a leak-preventing barrier at the ends to prevent leakage at the waist. The barrier is a strip of thin film which is affixed between the topsheet and the backsheet along a single line at the perimeter of the diaper.

U.S. Pat. No. 3,693,622 which issued to J. L. Jones, Sr. on Sept. 26, 1972 teaches a waste fluid absorption device in which the periphery of the absorbent core is treated with a liquid repellant composition which renders the periphery liquid-impermeable. U.S. Pat. No. 3,799,167 which issued to A. H. Miller et al on Mar. 26, 1974 is similar in concept to the aforementioned Jones patent in that the periphery of the absorbent article is rendered liquid-impermeable by treatment with a waterproofing composition. Miller et al, however, apply the waterproofing composition to the periphery of the topsheet rather than to the periphery of the absorbent core.

The disposable absorbent articles of the prior art lack the aspects of the present invention whereby a reduction in liquid leakage is obtained by providing liquid impermeable barrier members which are affixed to compacted portions of the topsheet.

It is therefore an object of the present invention to provide an absorbent article having improved liquid containment characteristics.

A further object of the present invention is to provide an absorbent article having liquid impermeable barrier members.

An additional object of the present invention is to provide an absorbent article having barrier members which are affixed to compacted portions of the topsheet.

These and other objects of the invention will be more readily apparent when considered in reference to the following description and when taken in connection with the accompanying drawings.

SUMMARY OF THE INVENTION

According to the present invention, a disposable absorbent article such as a diaper is manufactured such that an absorbent core is encased between a liquid permeable topsheet and a liquid impermeable backsheet. The disposable absorbent article is provided with at least one liquid impermeable barrier member at the edge of the absorbent core. However, a multiplicity of liquid impermeable barrier members may be provided at the edge of the absorbent core.

The barrier member comprises an outward portion projecting from the edge of the absorbent core away from the center of the disposable absorbent article, and an inward portion interposed between the topsheet and the absorbent core. A first end of the barrier member is preferably affixed to the backsheet.

The topsheet has liquid migration resistant segments corresponding to each barrier member. The liquid migration resistant segments each comprise a compacted portion which is affixed to the inward portion of a barrier member with a liquid retarding bond. The compacted portion alters the flow pattern of liquid as it moves from the point of discharge toward the edge of the absorbent core. The desired affect of the compacted portion may be achieved, for example, by densifying the compacted portion to reduce the intersticial void volume thereby causing the compacted portion to exhibit a greater capillary attraction for liquid than the uncompacted portions of the topsheet. Thus, by configuring the compacted portion so as to redirect the liquid away from the edge of the absorbent core leakage is reduced.

DESCRIPTION OF A PREFERRED EMBODIMENT

Referring now to the figures, there is shown a preferred embodiment of the present invention as it would be used in a disposable absorbent article and, in particular, as it would be used in a disposable diaper. As used herein, the term "disposable absorbent article" refers to articles which absorb and contain liquid, and more specifically refers to articles which are placed against or in proximity to the human body to absorb and contain the various liquids discharged therefrom (e.g., blood, menses, urine, etc.), and further which articles are intended to be discarded after a single use (i.e., they are not intended to be laundered or otherwise restored and reused). A "diaper" is a garment generally worn by infants and incontinent persons, which is drawn up between the legs and fastened about the waist of the user. It should be understood, however, that the present invention is also applicable for use in other disposable absorbent articles such as bandages, bed pads, catamenial pads, and the like.

Figure 1:
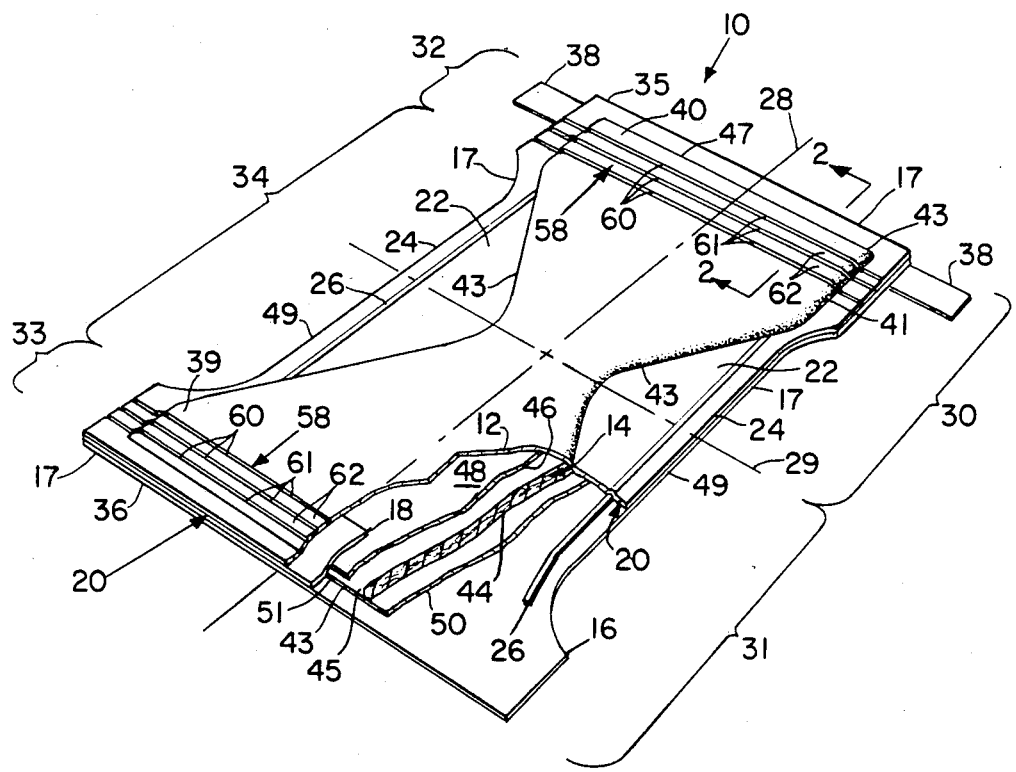
FIG. 1 is a partially cutaway perspective view of a disposable diaper incorporating the present invention.

FIG. 1 is a partially cut-away view of the disposable diaper 10 of the present invention prior to its being folded and placed on the diaper wearer. As seen in FIG. 1, a preferred disposable diaper 10 basically comprises a liquid permeable topsheet 12, an absorbent core 14, a liquid impermeable backsheet 16, and a barrier member 18. While the topsheet 12, absorbent core 14, and backsheet 16 may be assembled in a variety of well known configurations, a preferred disposable diaper assembly is described generally in U.S. Pat. No. 3,860,003 entitled CONTRACTABLE SIDE PORTIONS FOR DISPOSABLE DIAPER which issued to K. B. Buell on Jan. 14, 1975, which patent is incorporated herein by reference.

Figure 2:
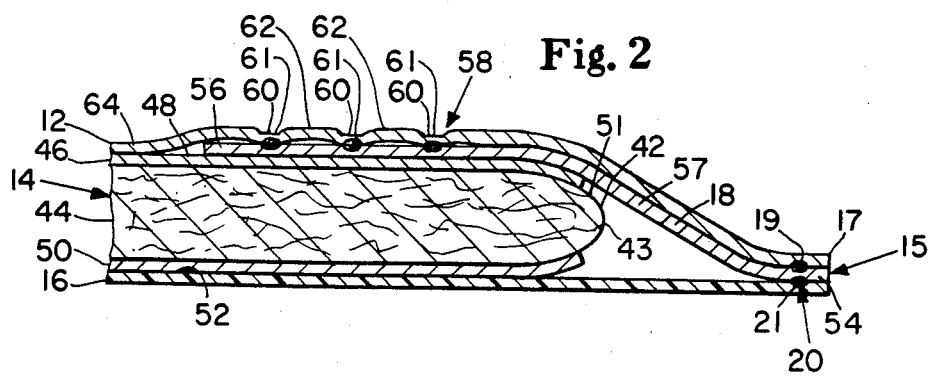
FIG. 2 is a cross-sectional view of the diaper of FIG. 1 taken along line 2—2.

FIGS. 1 and 2 show a preferred embodiment of the diaper 10, in which the topsheet 12 and the backsheet 16 are coextensive and have length and width dimensions generally larger than those of the absorbent core 14. The topsheet 12 is superposed on the backsheet 16 thereby forming a peripheral edge 17. The peripheral edge 17 defines the outer periphery or in other words the outer extent of the diaper 10 and encircles the absorbent core 14. The topsheet 12 is affixed to the backsheet 16 in any suitable manner using an attachment means 15 (FIG. 2). In a preferred embodiment the attachment means 15 comprises a peripheral seam 20 which may be a continuous band of hot melt adhesive placed around the entire marginal portion of the diaper 10 thereby encasing the absorbent core 14 between the topsheet 12 and the backsheet 16. A suitable hot melt adhesive is Eastobond A-3 as manufactured by the Eastman Chemical Products Company of Kingsport, Tenn. The attachment means 15 may take on many alternative configurations. For example, the topsheet 12 and the backsheet 16 may each be affixed to an intermediate member, such as the barrier member 18, rather than being affixed directly to each other.

A preferred embodiment of the diaper 10 has a side flap 22 on each longitudinal side 24 of the diaper 10. For the purpose of providing an elasticized contractible line within the side flap 22, an elastic member 26 is associated with each side flap 22, thereby providing an elastically contractible edge 49 in each side flap 22. More detailed and specific information concerning the side flaps 22 and the elastic member 26 is set forth in the hereinbefore referenced U.S. Pat. No. 3,860,003.

The disposable diaper 10 has a longitudinal centerline 28, a lateral centerline 29, a back portion 30, a front portion 31, a back waist portion 32, a front waist portion 33, and a crotch area 34. Further, the peripheral edge 17 comprises a back edge 35 and a front edge 36 traveling the distance between the longitudinal sides 24 at either end of the disposable diaper 10.

The back portion 30, in general, is that part of the diaper from the lateral centerline 29 to the back edge 35 of the diaper 10 and which when the diaper 10 is worn contacts the back of the infant. The front portion 31, in general, is that portion of the diaper 10 from the lateral centerline 29 to the front edge 36 of the diaper 10 and which when the diaper 10 is worn contacts the front of the infant. The back waist portion 32 is that marginal portion of the diaper 10 adjacent to back edge 35. The front waist portion 33 is that marginal portion of the diaper 10 adjacent to the front edge 36. The back and front waist portions 32 and 33, respectively, cooperate with each other when the diaper 10 is fitted on and attached to an infant to encircle the infant's waist and hold the diaper 10 on the infant. The back waist portion 32 and the front waist portion 33 each have a width which extends from the back edge 35 and the front edge 36, respectively, toward the lateral center line 29 a distance of approximately 1 inch to $2\frac{1}{2}$ inches (2.5 cm. to 6.4 cm.) and each has a length which extends transversely across the diaper 10 at the back edge 35 and at the front edge 36, respectively. The depth of the back and front waist portions, 32 and 33 respectively, is established primarily by and includes the diaper fastening means for affixing the diaper around the waist of the infant. An acceptable fastening means is an adhesive fastening tape 38 as is well known in the disposable diaper art.

The crotch area 34 of the diaper 10 is that area of the diaper which is generally located directly between the legs and around the lower portion of an infant when the diaper 10 is worn and is approximately centered on the lateral centerline 29.

The absorbent core 14 may be manufactured in a wide variety of sizes and from a wide variety of absorbent materials which are commonly used in disposable absorbent articles and which are capable of absorbing and retaining liquids. While comminuted wood pulp, generally referred to as airfelt, is preferred for the manufacture of the absorbent core 14, other liquid absorbent materials such as foams, a multiplicity of plies of creped cellulose wadding, or any equivalent material may also be used. The total absorbent capacity of the absorbent core 14 should, however, be compatible with the design liquid loadings in the intended use of the absorbent article.

The preferred embodiment illustrated in FIG. 1 has an hourglass shaped absorbent core 14 wherein the absorbent core 14 in the back and front waist portions 32 and 33 respectively is wider than the absorbent core 14 in the crotch area 34, thereby forming ears 39, 40, 41, and a fourth ear which is not shown, at the corners of the absorbent core 14. The preferred embodiment illustrated in FIG. 1 is intended to be worn by infants ranging in weight from 12 pounds to about 26 pounds (5 kgs. to about 12 kgs.). The absorbent core 14 is, therefore, a pad of airfelt approximately 16 inches (40.6 cm.) long when measured along the longitudinal centerline 28, having a width of approximately 12 inches (31.9 cm.) across back and front waist portions 32 and 33, respectively, and having a width of approximately 4 inches (10.2 cm.) across the crotch area 34 of the diaper 10. The absorptive capacity of the airfelt used for the absorbent core 14 is sufficient to absorb and retain approximately from 8 to 16 grams of water per gram of absorbent. Accordingly, the airfelt used in the preferred embodiment shown in FIG. 1 weighs approximately from 30 to 56 grams. It should be understood, however, that the size, shape, and total absorbent capacity of the absorbent core 14 may be varied to accommodate diaper wearers ranging from infants to adults. Therefore, other dimensions and even other shapes (e.g., rectangular) may also be used for the absorbent core 14.

The absorbent core 14 has a core edge 43 which defines the outer extent of the absorbent core 14 and which comprises a multiplicity of core edge segments. A core edge segment is a portion of the core edge 43. Preferably, the core edge 43 comprises a front end segment 45 which is the core edge segment traversing the end of the absorbent core 14 at the front waist portion 33 of the diaper 10 and a back end segment 47 which is the core edge segment traversing the end of the absorbent core 14 at the back waist portion 32 of the diaper 10. The core edge 43 has a core edge surface 42 (FIG. 2) which faces away from the center of the absorbent core 14.

As best seen in FIG. 2, a preferred absorbent core 14 comprises an absorbent layer 44 and a first tissue layer 46 which forms a first opposed surface 48 of the absorbent core 14 and a second tissue layer 50 which forms a second opposed surface 52 of the absorbent core 14. The core edge surface 42 joins first and second opposed surfaces 48 and 52. Thus, the outer surfaces of the absorbent core 14 are defined by the first opposed surface 48, the second opposed surface 52 and by the core edge surface 42.

The absorbent layer 44 is preferably comminuted wood pulp as hereinbefore described. The first and second tissue layers 46 and 50 improve the tensile strength of the absorbent layer 44 and reduce the tendency of the absorbent layer 44 to lump or ball when wetted. While a number of materials and manufacturing techniques may be used to manufacture the tissue layers 46 and 50, satisfactory results have been obtained with sheets of wet strength tissue paper having a basis weight of about 12 pounds per 3,000 square feet (19 gms. per square meter) and having an air permeability of about 100 cubic feet per minute per square ft. (30.5 cubic meters per minute per square meter) over a ½ inch (12.8 mm.) water pressure drop. While the tissue layers 46 and 50 are preferably coterminous with the absorbent layer 44, they may have different dimensions, a different configuration, or may be omitted entirely.

The second tissue layer 50 of the absorbent core 14 is superposed on backsheet 16 and is preferably attached thereto by attachment means such as those well known in the art. Accordingly, the absorbent core 14 can be secured to the backsheet 16 by a uniform continuous layer of adhesive, a patterned layer of adhesive or a number of separated lines or spots of adhesive. An adhesive which has been found to be satisfactory is manufactured by Eastman Chemical Products Company of Kingsport, Tenn. and marketed under the tradename Eastobond A-3.

The backsheet 16 is impermeable to liquids and prevents liquids absorbed by the absorbent core 14 from wetting the undergarments, clothing, bedding, and other objects which contact the wearer of the disposable diaper 10. Preferably the backsheet 16 is a polyethylene film of from about 0.0005 to about 0.002 inches (about 0.0012 to about 0.051 mm.) thick, although other flexible, liquid impermeable materials may also be used. As used herein, the term "flexible" refers to materials which are compliant and which readily conform to the shape and contours of the human body. A suitable polyethylene film is manufactured by Monsanto Chemical Company and marketed in the trade as film No. 8020.

In a preferred embodiment, the backsheet 16 has a modified hourglass configuration extending beyond the core edge 43 a distance of approximately ½ inch to 1 inch (1.3 cm. to 2.5 cm.). Along the longitudinal sides 24 of the diaper 10, the backsheet 16 extends beyond and is generally parallel to the core edge 43. As the absorbent core 14 gets narrower towards the crotch area 34, the edge of the backsheet 16 is substantially linear and parallel to the longitudinal centerline 28 so that the backsheet 16 is wider than the absorbent core 14 and the side flap 22 becomes increasingly wider until the lateral centerline 29 is reached. This linear portion on the backsheet 16 forms the contractible edge 49 of the side flap 22. The linear portion of the lateral edge of the backsheet 16 is generally between 5 inches and 12 inches (between 12 and 30 cm.) long and for the diaper 10 of the preferred embodiment illustrated in FIG. 1, is about 9 inches (23 cm.) long. The backsheet 16 is preferably embossed and/or matte finished to provide a more cloth-like appearance. Further, the backsheet 16 may be perforated to permit vapors to escape from the absorbent core 14, provided liquid is not allowed to pass from the absorbent core 14 through the backsheet 16.

The topsheet 12 is compliant, soft feeling, and non-irritating to the wearer's skin. Further, the topsheet 12 is fibrous and liquid permeable, permitting liquids to readily penetrate through its thickness. A suitable topsheet 12 may be manufactured from a wide range of materials such as natural fibers (e.g., wood or cotton fibers) synthetic fibers (e.g., polyester or polypropylene) or a combination thereof and prevents the wearer of the diaper 10 from contacting the absorbent core 14. Alternatively, the topsheet 12 may be a fiber-like foam such as the reticulated foams which are well known in the art.

A particularly preferred topsheet 12 comprises by weight about 65 percent staple length polyester fibers having a denier of about 1.5, such as Kodel Type 411 polyester fiber marketed by Tennessee Eastman Corporation of Kingsport, Tenn., about 15 percent staple length crimped rayon fibers having a denier of approximately 1.5; and about 20 percent acrylic copolymer binder such as Celanese CPE 8335 marketed by Celanese Corporation of Charlotte, N.C. As used herein, the term "staple length fibers" refers to those fibers having a length of at least 0.625 inches (15.9 mm.).

Clearly, there are a number of manufacturing techniques which may be utilized to manufacture the topsheet 12. For example, the topsheet 12 may be woven, nonwoven, spunbonded, carded, or the like. A preferred topsheet 12 is carded, saturated with a binder solution, dried and cured by means well know to those skilled in the art. Preferably, the topsheet 12 has a basis weight range of from about 18 to about 30 grams per square yard, a minimum wet tensile strength of at least 400 grams per cm. in the machine direction and at least about 55 grams per cm. in the cross-machine direction.

A barrier member 18 is provided at each portion of the core edge 43 from which it is desired to reduce liquid leakage. Thus, a barrier member 18 may be positioned at a portion of the core edge 43 (e.g. the front end segment 45 or the back end segment 47) or at the entire core edge 43. Of course, a multiplicity of barrier members 18 may be provided at various portions of the core edge 43 or at the entire core edge 43.

Each portion of the core edge 43 provided with a barrier member 18 is a barriered core edge segment 51. From the foregoing it is clear that the diaper 10 may have one or a multiplicity of barrier members 18 and barriered core edge segments 51.

In the preferred embodiment illustrated in FIGS. 1 and 2 a barrier member 18 is positioned at both the front end segment 45 and at the back end segment 47 of the absorbent core 14 and both barrier members 18 are intended to prevent premature leakage of the liquid absorbed by the absorbent core 14 from the edges 35 and 36 of the diaper 10. As hereinbefore stated, however, additional barrier members 18 may be provided at other portions of the core edge 43. Since the basic construction of the back edge 35 will be generally the same as that of the front edge 36, the basic construction of the back edge 35 only will be described. It should be understood, however, that the front edge 36 is preferably also constructed in accordance with the following discussion as are other sections of the core edge 43 which are provided with a barrier member 18.

While the barrier member 18 may be a unitary part of the backsheet 16, it is preferably a separate element which may be affixed to the backsheet 16 and made integral therewith. The barrier member 18 is preferably manufactured from a thin, flexible, liquid impermeable material such as polyethylene or polypropylene film. As used herein, the term "unitary" refers to a barrier member 18 and a backsheet 16 which are a single piece of material that is neither divided nor discontinuous. The term "integral" refers to a barrier member 18 which is a discrete separate element affixed to the backsheet 16. The term "liquid impermeable" includes materials which retard the flow of liquid through the thickness of the material in at least one direction.

Materials similar to those used for the liquid impermeable backsheet 16 are generally suitable for use as the barrier member 18. A preferred film for use as the barrier member 18 has a sheet tensile strength of at least about 1 pound per inch of width (180 gm/cm of width) in the machine direction of the barrier member 18 and a sheet tensile strength of at least about 0.5 pounds per inch of width (90 gm/cm of width) in the cross-machine direction of the barrier member 18, thereby providing the diaper 10 with improved structural integrity when the barrier member 18 is placed at the edges 35 and 36, especially during fitting and placement of the diaper 10 on the infant. In addition, a most preferred film for use as the barrier member 18 has a surface energy of at least about 30 dynes/sq. cm. In a preferred embodiment, a heat sealable film such as manufactured by Dow Chemical Company of Midland, Mich. and marketed under the tradename CUF-804 was used for the barrier member 18.

Referring now to FIG. 2, it can be seen that a barrier member 18 has an inward portion 56, and an outward portion 57. The inward position 56 is interposed between the topsheet 12 and the absorbent core 14 extending from the barriered core edge segment 51 generally toward the center of the absorbent core 14 a distance sufficient to provide protection against leakage of liquid from the portion of the first opposed surface 48 in proximity to the barriered core edge segment 51. It has been found that extending the inward portion 56 a distance of from about 0.25 to about 3.5 inches (about 0.6 to about 8.9 cm.) from the barriered core edge segment 51 generally toward the center of the absorbent core 14 is sufficient to provide protection against liquid leakage.

The outward portion 57 of the barrier member 18 extends from the barriered core edge segment 51 and generally provides protection against leakage of liquid emanating from the edge surface 42 of the barriered core edge segment 51. As used herein, the term "extends" includes but is not limited to embodiments in which the outward portion 57 overlays the core edge 43 or is wrapped around the core edge 43 and interposed between the backsheet 16 and the absorbent core 14 or is extended away from the core edge 43 toward the peripheral edge 17 of the diaper 10. In the preferred embodiment shown in FIGS. 1 and 2 the outward portion 57 has a first end 54 which is preferably affixed to the backsheet 16 thereby capping the barriered core edge segment 51. In the preferred embodiment illustrated in FIGS. 1 and 2, the peripheral seam 20 is used to affix the first end 54 directly to the backsheet 16. Accordingly, at the back edge 35 the peripheral seam 20 comprises a first seam 19 which affixes the topsheet 12 to the barrier member 18 and a second seam 21 which affixes the barrier member 18 to the backsheet 16 and the attachment means 15 therefore comprises first seam 19, second seam 21 and first end 54.

The topsheet 12 has liquid migration resistant segments 58 corresponding to each barrier member 18. The liquid migration resistant segments 58 comprise a compacted portion 60 which alters the flow pattern of liquid as it moves from the point of discharge toward the core edge 43 of the absorbent core 14. The desired effect of the compacted portion 60 may be achieved in many ways such as by filling the intersticial voids of the compacted portion 60 with an adhesive or other liquid impermeable material. In this manner, the compacted portion 60 is made to act as a barrier to the movement of liquid. In a preferred embodiment, however, the compacted portion 60 is compressed or densified relative to the other portions of the topsheet 12, which portions for convenience are designated uncompacted portions 64 (FIG. 2). In other words, both the spacing between fibers and the interstitial void volume are reduced in the compacted portion 60 to an extent sufficient to cause the compacted portion 60 to exhibit a greater capillary attraction for liquid than the uncompacted portion 64. Thus, liquid contacting the compacted portion 60 will wick into and throught the compacted portion 60. The compacted portion 60, therefore, alters the liquid flow pattern and by configuring the compacted portion 60 as hereinafter described liquid is redirected away from those parts of the diaper from which leakage may occur.

The ratio of the caliper of the uncompacted portion 64 of the topsheet 12 to the caliper of the compacted portion 60 is at least about 1.5:1 and preferably at least about 2.0:1. Most preferably, the ratio of the caliper of the uncompacted portion 64 to the caliper of the compacted portion 60 is at least about 4:1. It should be understood the term "caliper" refers to thickness only and does not in any way refer to the relative elevations of the compacted and uncompacted portions 60 and 64. Therefore, the compacted portion 60 may have a higher elevation than the uncompacted portion 64, or as shown in FIG. 2 the compacted portion 60 may be depressed below the surface of the uncompacted portion 64.

Many procedures are suitable for determining the ratio of the caliper of the uncompacted portion 64 to the caliper of the compacted portion 60. For example, a simple optical procedure may be used whereby a strip of the topsheet is cut perpendicular to the compacted portion 60. By viewing the edge of the strip through a microscope having a calibrated eyepiece, the calipers of the uncompacted portion 64 and of the compacted portion 60 can be determined. From the individual calipers, the ratio of the calipers is easily calculated.

The compacted portion 60 of the topsheet 12 is affixed to a barrier member 18 using any suitable means which will provide a liquid retarding bond between the topsheet 12 and the barrier member 18. Thus, liquid migration along the interfacial junction between the topsheet 12 and the barrier member 18 is retarded and is preferably prevented. In a preferred embodiment, heat sealing along the compacted portion 60 as is well known in the art was used and found to be satisfactory. The use of heat sealing techniques to affix the compacted portion 60 to the barrier member 18 has the additional advantage of compressing the compacted portion 60 at the same time it is affixed to the barrier member 18.

A compacted portion 60 corresponds to each barrier member 18 and is intended to retard and preferably to prevent liquid which flows along the surface of the topsheet 12, liquid which is absorbed by the topsheet 12 and liquid which flows in the capillary channel formed between the topsheet 12 and the skin of the wearer from wetting the vicinity surrounding the diaper 10. Accordingly, the compacted portion 60 is configured so as to render the path followed by the above identified liquids tortuous and preferably impassible. Thus, each compacted portion 60 preferably, comprises a multiplicity of continuous bands 61 defining reservoirs 62 therebetween. The reservoirs 62 are preferably neither compacted nor affixed to the barrier member 18.

In the preferred embodiment illustrated in FIGS. 1 and 2, a compacted portion 60 comprising a multiplicity of continuous bands 61 is provided at both the front edge 36 and at the back edge 35 corresponding to each of the barrier members 18. The bands 61 are straight lines which are generally parallel to the edges 35 and 36 and which traverse the entire distance between the longitudinal sides 24.

The combination of bands 61 and reservoirs 62 promote a redirection and absorption of liquids so that the liquids will not reach a point from which they can wet the vicinity surrounding the diaper 10. The bands 61 have a width of at least about 0.01 inches (0.25 mm) and preferably at least about 0.06 inches (1.59 mm) while the reservoirs 62 have a width of at least about 0.03 inches (0.79 mm) and preferably at least about 0.09 inches (2.38 mm). The narrower the width of bands 61 and reservoirs 62 the more readily liquid will bridge them without being redirected or absorbed.

The compacted portion 60 may take on a variety of configurations such as an array of discrete areas. For example, the array of discrete areas may comprise a multiplicity of spaced circles, dashes, or ovals arranged in either a random or regular pattern. Alternatively, the compacted portion 60 may comprise a multiplicity of bands having gaps or spaces arranged so that the gaps or spaces in adjoining lines do not coincide thereby providing a tortuous path from the point of liquid discharge to a point from which the liquid can wet the vicinity surrounding the diaper 10. Further, the compacted portion 60 may comprise a multiplicity of bands 61 which may be rectilinear, curvilinear, straight, or curved and which may have parallel sides forming a band 61 of uniform width or may have nonparallel sides forming a band 61 of varying width. As hereinbefore stated, a compacted portion 60 corresponds to each barrier member 18. Diaper 10 may, therefore, have a multiplicity of compacted portions 60 each of which comprises a multiplicity of bands 61.

The diaper 10 of the present invention exhibits improved leakage containment about the waist of the wearer. As can be seen in Table I, Sample A did not have a barrier member 18 and failed at a liquid loading of 67 ml. The addition of the barrier member 18 to the configuration of Sample A raised the liquid loading at failure to 125 ml. A further significant improvement, however, is achieved by providing the topsheet 12 with a compacted portion 60 which is affixed to the inward portion 56 of the barrier member 18. Accordingly, the liquid loading at failure of Sample C is 150 ml. Sample D was provided with a compacted portion 60 but not with a barrier member 18 and failed at a liquid loading of 50 ml.

TABLE I

| Liquid Loading at Failure for Various Diaper Configurations | |
|---|---|
| Sample[1] | Liquid Loading at Failure (ml.) |
| A[2] | 67 |
| B[3] | 125 |
| C[4] | 150 |
| D[5] | 50 |

Notes:
[1]Samples A, B, and C were all constructed of the same material as follows: Topsheet - carded polyester fibers having 1½ denser fibers with 20% acrylic binder copolymer and weighing 20 gm/sq. yd.; Back-sheet - polyethylene sheet having a caliper of 0.001 inches; absorbent core - 43 grams of airfelt; barrier member - polyethylene film (CUF-804) extending 1.375 inches from the perimeter of the absorbent core toward the lateral centerline. The barrier members were provided at both front and back end segments; compacted portions - 3 straight lines about ⅛ inch wide spaced about ¼ inch apart the ratio of the caliper of the uncompacted topsheet to the caliper of the compacted portions being about 5:1.
[2]Sample A was constructed in general in accordance with the foregoing discussion (Note 1) except that the barrier member 18 and the compacted portions 58 were omitted.
[3]Sample B was constructed in the same manner and configuration as Sample A except that the barrier member 18 was provided. The compacted portions 58 were, however, omitted and the topsheet 12 was not affixed to the inward portion 56 of the barrier member 18.
[4]Sample C was constructed in the same manner and configuration as Sample B and was provided with the compacted portions 58 which were affixed to the inward portion 56 of the barrier member 18.
[5]Sample D was constructed in the same manner and configuration as Sample A except that the compacted portions 58 were provided.

The data presented in Table I was generated using the following procedure. The sample diaper is placed on a model simulating an infant weighing about 3 kilograms and having a circumference of about 43 cm. when the infant is lying on its stomach. Since only leakage at the waist of the diaper is being investigated, it is necessary that only the waist portion be simulated. A 10 cm. square piece of filter paper such as #40 Whatman filter paper, is placed so that it overlays about 6.4 mm. of the absorbent core of the sample. The filter paper is marked with water soluble ink which changes color when wet to indicate when the diaper has failed.

A urine simulating liquid is then introduced between the model and the front of the diaper sample at a point approximately 3.5 inches from the front edge 45 of the absorbent core 16 at 10 minute intervals and the amount of liquid introduced at failure is the liquid loading at failure. For the data presented in Table I, an initial loading of 50 ml. of a 45 dyne urine simulating liquid was used with additional loadings of 25 ml. each 10 minutes.

While not wishing to be bound by any one theory describing the operation of the present invention, it is believed that the improvement in liquid containment is achieved in the manner now to be described.

In use, the diaper 10 is placed between the legs of the diaper wearer and the back waist portion 32 and the front waist portion 33 are drawn and fastened about the diaper wearer's waist using any suitable means such as the adhesive tapes 38. When the diaper 10 of the present invention is applied to an infant, it exhibits improved liquid containment. As urine is discharged onto the topsheet 12, some of the urine penetrates the topsheet 12 where it is absorbed by the absorbent core 14, some of the urine flows on the surface of the topsheet 12, some of the urine is absorbed by and wicks laterally through the topsheet 12 and some of the urine flows in the capillary channel formed at the interface between the topsheet 12 and the skin of the wearer.

The absorbed urine migrates throughout the absorbent core 14 moving from the point of discharge (i.e., the crotch area 34) toward the back edge 35 and the front edge 36. Because the liquid impermeable barrier member 18 is affixed to the liquid impermeable backsheet 16 by means of the second seam 21, thereby forming a liquid impermeable cap over the core edge 43, the absorbed urine is prevented from wetting the articles such as bedding and clothing, which contact the edges 35 and 36 of the diaper 10. In addition, because the barrier member 18 is affixed to the topsheet 12 along compacted portions 60, liquid is prevented from flowing in the capillary passage created at the interface between the topsheet 12 and the barrier member 18.

The surface urine, likewise, moves from the point of discharge toward the back edge 35 and the front edge 36 on the surface of the topsheet 12. As the surface urine approaches the back and front edges 35 and 36, respectively, a compacted portion 60 will be contacted. Having a greater capillary attraction for liquid than does the generally uncompacted topsheet 12, the compacted portion 60 will cause the surface urine to be absorbed by and to wick laterally along the band 61, rather than continue to flow toward the edges 35 and 36 of the diaper 10. Having once entered the compacted portion 60 the liquid will tend to be held in the compacted portion 60 because the compacted portion 60 has a higher capillary attraction for liquid than does the adjacent uncompacted topsheet 12. As local areas of the band 61 become saturated, the surface urine may overcome the retarding effect of the band 61 and may flow into and be contained by the reservoir 62. As the reservoir 62, in turn, becomes saturated, the surface urine will encounter a second band 61 and again will be absorbed by and wick laterally along the band 61. In this manner, liquid is retarded or prevented from reaching the edges 35 and 36 of the diaper 10.

Liquid is retarded from flowing along the capillary channel formed between the topsheet 12 and the skin of the wearer by the elevation difference between the compacted portion 60 and the uncompacted portion 64 of the topsheet 12 present in the preferred embodiment illustrated in FIGS. 1 and 2. Thus, liquid flowing between the wearers skin and the topsheet 12 will encounter a band 61 which in the preferred embodiment illustrate in FIGS. 1 and 2 is depressed below the plane defined by the surface of the uncompacted portion of the topsheet and is therefore not in contact with the wearers skin. Thus a discontinuity is created between the wearer's skin and the topsheet 12. This discontinuity interrupts the capillary channel and retards further liquid flow toward the back and front edges 35 and 36.

Finally, urine which is absorbed intersticially by the topsheet 12 wicks laterally through the topsheet 12 toward the back and front edges 35 and 36. As in the instance of the surface urine, the urine absorbed by the topsheet 12 encounters a compacted portion 60 which causes the urine to wick laterally along the band 61. The urine absorbed by the topsheet is thereby prevented from reaching the back or front edges 35 and 36.

It will be understood by those skilled in the art that the present invention has been described with reference to an exemplary embodiment and that variations and modifications can be effected in the described embodiment without departing from the spirit and scope of the invention.

For example, since urine is generally discharged onto the front portion 31, the barrier member 18 may be provided at the front edge 36 only. In addition, construction techniques other than those expressly disclosed may be used. For example, the peripheral seam 20 may be formed using ultrasonic bonding procedures. Further, the peripheral seam 20 may be a discontinuous series of closely spaced dots, ovals, dashes or longitudinally running lines.

Figure 3:
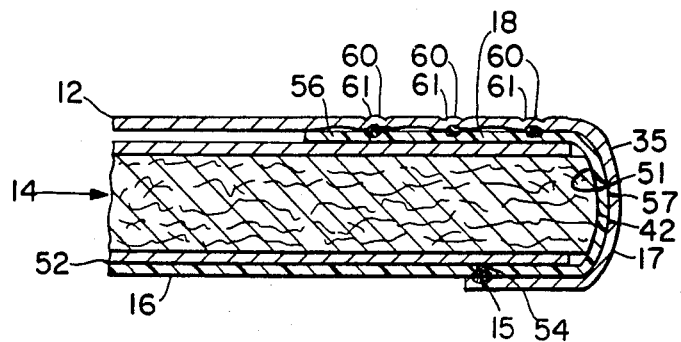
FIG. 3 is a cross-sectional view of an alternative diaper construction taken along a line corresponding to line 2—2 of FIG. 1.

In an alternatively preferred embodiment, the barrier member 18 may be unitary with the backsheet 16. As shown in FIG. 3, the backsheet 16 overlays the second opposed surface 52 of the absorbent core 14 and the barrier member 18 is unitary therewith. The topsheet 12 overlays the barrier member 18 and is affixed to the backsheet 16 by attachment means 15 which when the backsheet 16 and the barrier member 18 are unitary, defines the first end 54 of the barrier member 18. The inward portion 56 of the barrier member 18 is interposed between the topsheet 12 and the absorbent core 14 while the outward portion 57 projects from the barriered core edge segment 51 away from the center of the absorbent core 14 and overlays the core edge surface 42. The compacted portion 60 comprises a multiplicity of bands 61 which are affixed to inward position 56 of the barrier member 18 as hereinbefore described. In the embodiment illustrated in FIG. 3, the barrier member 18 froms the peripheral edge 17 at the back end 35.

In another alternatively preferred embodiment, a barrier member 18 is provided along each longitudinal side 24.

Figure 4:
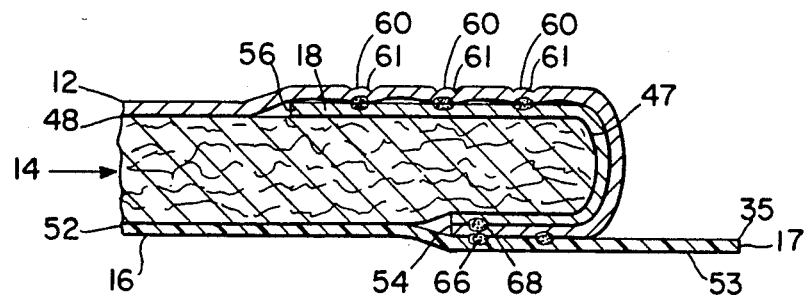
FIG. 4 is a cross-sectional view of another alternative diaper construction taken along a line corresponding to line 2—2 of FIG. 1.

In still another alternatively preferred embodiment, a barrier member 18 is affixed to the backsheet 16 through an interposed member. As shown in FIG. 4, the topsheet 12 overlays the back end segment 47 of the absorbent core 14 and is interposed between the backsheet 16 and the second opposed surface 52 of the absorbent core 14. The barrier member 18 has an inward portion 56 interposed between the topsheet 12 and first opposed surface 48 of absorbent core 14. The first end 54 of the barrier member is affixed to the topsheet 12 along seam 68 and the topsheet 12 is affixed to the backsheet 16 along seam 66. The topsheet 12 is affixed to the barrier member 18 along the compacted portion 60 which comprises a multiplicity of bands 61. In the embodiment illustrated in FIG. 4, the backsheet 16 extends beyond back end segment 47 forming flap 53. The edge of flap 53 comprises a segment of the peripheral edge 17 at the back end 35.

What is claimed is:

1. A disposable diaper comprising:
   a fibrous liquid permeable topsheet;
   a liquid impermeable backsheet;
   an attachment means for affixing said topsheet to said backsheet;
   an absorbent core means for absorbing liquids, said absorbent core means being encased between said topsheet and said backsheet and having a core edge, said absorbent core means having a barriered core edge segment comprising at least a segment of said core edge;
   a liquid impermeable barrier member having an outward portion extending from said barriered core edge segment and having an inward portion interposed between said topsheet and said absorbent core means, said topsheet having a liquid migration resistant segment comprising a compacted portion affixed to said inward portion of said barrier member, said compacted portion comprising a multiplicity of continuous bands.

2. A disposable diaper comprising:
   a fibrous liquid permeable topsheet;
   a liquid impermeable backsheet;
   an attachment means for affixing said topsheet to said backsheet;
   an absorbent core means for absorbing liquids, said absorbent core means being encased between said topsheet and said backsheet and having a core edge, said absorbent core means having a barriered core edge segment comprising at least a segment of said core edge;
   a liquid impermeable barrier member having an outward portion extending from said barriered core edge segment and having an inward portion interposed between said topsheet and said absorbent core means, said topsheet having a liquid migration resistant segment comprising a compacted portion affixed to said inward portion of said barrier member, said compacted portion comprising an array of discrete areas.

3. The disposable diaper of claim 1 or 2 wherein said barriered core edge segment comprises a front end segment, said inward portion of said barrier member overlaying said absorbent core means adjacent to said front end segment.

4. The disposable diaper of claim 1 or 2 wherein said outward portion of said barrier member has a first end affixed to said backsheet.

5. The disposable diaper of claim 1, or 2 wherein said topsheet has an uncompacted portion and the ratio of the caliper of said uncompacted portion to the caliper of said compacted portion is at least about 1.5:1.

6. The disposable diaper of claim 1 having a multiplicity of reservoirs between said bands.

7. The disposable diaper of claim 6 wherein said continuous bands have a width of at least about 0.01 inches and said reservoirs have a width of at least about 0.03 inches.

8. The disposable diaper of claim 1 or 2 wherein said barrier member has a sheet tensile strength of at least about 1 pound per inch of width in the machine direction and at least about 0.5 pounds per inch of width in the cross machine direction.

9. The disposable diaper of claim 8 wherein said barrier member has a surface energy of at least about 30 dynes per square centimeter.

10. A disposable absorbent article comprising:
    a fibrous liquid permeable topsheet;
    a liquid impermeable backsheet;
    an attachment means for affixing said topsheet to said backsheet;
    an absorbent core means for absorbing liquids, said absorbent core means being encased between said topsheet and said backsheet and having a core edge, said absorbent core means having a barriered core edge segment comprising at least a segment of said core edge;
    a liquid impermeable barrier member having an outward portion extending from said barriered core edge segment and having an inward portion interposed between said topsheet and said absorbent core means, said topsheet having a liquid migration resistant segment comprising a compacted portion affixed to said inward portion of said barrier member, said compacted portion comprising a multiplicity of continuous bands.

* * * * *